(12) United States Patent
Tengler et al.

(10) Patent No.: US 11,166,947 B2
(45) Date of Patent: Nov. 9, 2021

(54) EFFECTIVE DOSING OF A CHILD FOR THE TREATMENT OF ADHD WITH METHYLPHENIDATE

(71) Applicant: Neos Therapeutics, LP, Grand Prairie, TX (US)

(72) Inventors: Mark Tengler, Colleyville, TX (US); Nathan Teuscher, Trophy Club, TX (US)

(73) Assignee: Neos Therapeutics, LP, Grand Prairie, TX (US)

( * ) Notice: Subject to any disclaimer, the term of this patent is extended or adjusted under 35 U.S.C. 154(b) by 86 days.

(21) Appl. No.: 16/346,850

(22) PCT Filed: Oct. 31, 2017

(86) PCT No.: PCT/US2017/059256
§ 371 (c)(1),
(2) Date: May 1, 2019

(87) PCT Pub. No.: WO2018/085256
PCT Pub. Date: May 11, 2018

(65) Prior Publication Data
US 2019/0314356 A1    Oct. 17, 2019

Related U.S. Application Data

(60) Provisional application No. 62/415,884, filed on Nov. 1, 2016.

(51) Int. Cl.
| | | |
|---|---|---|
| *A61K 9/28* | (2006.01) | |
| *A61K 31/4458* | (2006.01) | |
| *A61P 25/00* | (2006.01) | |
| *A61K 9/00* | (2006.01) | |
| *A61K 9/50* | (2006.01) | |

(52) U.S. Cl.
CPC ........ *A61K 31/4458* (2013.01); *A61K 9/0053* (2013.01); *A61K 9/5084* (2013.01); *A61P 25/00* (2018.01)

(58) Field of Classification Search
None
See application file for complete search history.

(56) References Cited

U.S. PATENT DOCUMENTS

| | | | |
|---|---|---|---|
| 6,344,215 B1 | 2/2002 | Bettma et al. | |
| 8,709,491 B2 * | 4/2014 | Tengler | A61K 31/4458 424/501 |
| 2004/0197405 A1 | 10/2004 | Devane et al. | |
| 2006/0240105 A1 | 10/2006 | Devane et al. | |
| 2017/0196846 A1 * | 7/2017 | Adjei | A61K 31/4458 |

FOREIGN PATENT DOCUMENTS

| | | |
|---|---|---|
| WO | 2013003622 A1 | 1/2013 |
| WO | 2015188092 A1 | 12/2015 |

OTHER PUBLICATIONS

Derendorf, H. et al., "Modeling of pharmacokinetic/pharmacodynamic (PKPD) relationships: Concepts and Perspectives," Pharmaceutical Research (online) Feb. 1999, vol. 16, Issue 2, pp. 176-185.
Holford, N. H. et al., "Understanding the close-effect relationship—clinical-application of pharmacokinetic-pharmacodynamic models," Clinical Pharmcokinetics (online) Dec. 1981, vol. 6, Issue 6, pp. 429-453.
Sora et al., "An update on animal model studies of attention-deficit/hyperactivity disorder", Journal of Pharmacological Sciences, 2006, vol. 128: 8-12.

* cited by examiner

*Primary Examiner* — Susan T Tran
(74) *Attorney, Agent, or Firm* — Arent Fox LLP

(57) ABSTRACT

The present invention generally relates to treating attention-deficit disorders (e.g., ADHD) by providing an effective amount of an ADHD-effective agent to a patient in need thereof (e.g., a child).

2 Claims, 2 Drawing Sheets

EFFECTIVE DOSING OF A CHILD FOR THE TREATMENT OF ADHD WITH METHYLPHENIDATE

CROSS-REFERENCE TO RELATED APPLICATIONS

This application is U.S. National Phase of International Patent Application No. PCT/US2017/059256, filed Oct. 31, 2017, which claims priority to U.S. Provisional Patent Application No. 62/415,884, filed Nov. 1, 2016. The contents of each are hereby incorporated by reference in their entireties.

FIELD OF INVENTION

The present invention generally relates to treating attention-deficit disorders (e.g., ADHD) by providing an effective amount of an ADHD-effective agent to a patient in need thereof (e.g., a child).

BACKGROUND OF INVENTION

Field of the Invention

The invention relates to the treatment of Attention Deficit Hyperactivity Disorder (ADHD) by providing an effective amount of a dosage form. In particular, the invention provides a method for determining an effective amount of a methylphenidate formulation for administration to an individual.

Description of the Related Art

Many drug therapies use immediate-release oral dosage forms administered at spaced intervals to provide and maintain a desired therapeutic effect over a prolonged therapy period. For example, drugs used in treating Attention Deficit Disorder (ADD) and ADHD such as ADDERALL® and RITALIN® are administered two or three times a day.

For various reasons, subjects often experience difficulty complying with this administration schedule. Because ADD and ADHD are commonly diagnosed in children, determining the correct dose for individual patients is complicated by the variability in size as patients grow. The dosage regimen for children generally requires that at least one dose is administered during the school day. Children are typically not permitted to self-administer the drug at school. As such, authorized school personnel generally take on the responsibility for administering the drug to children during the school day. However, this approach raises issues of medical privacy and potential stigmatizing of the child by peers. In addition, the compliance issue becomes further complicated as transportation, storage and supply of the drug typically must be documented and/or monitored, and the schedules of the different parties involved, i.e., the child, the educators and the authorized school personnel, must be coordinated and accommodated. The unfortunate result is that doses may be given late or missed altogether resulting in decreased efficacy of the therapy.

Additionally, an effective method of dosing of drug therapies is currently described in the art as "titrating to effect". As shown in the prescription label for Daytrana®: "Dosage should be titrated to effect. Dose titration, final dosage, and wear time should be individualized according to the needs and response of the patient."

WO 2015/188092 describes that "the recommended dosing regimen begins with a titration regimen, starting the patient at a low dose for seven days, followed by weekly upward adjustments until the optimal response is reached." Additionally, the publication describes that "[i]t is known that clearance of methylphenidate is an important factor in reaching and maintaining therapeutically effective levels of MPH in a patient. However, it is also known that drug clearance in children and adults does not always correlate well with their total body weight." While the publication describes a dosing regimen for the specific formulation utilized, there is still a need for dosing regimens for other formulations of methylphenidate products.

SUMMARY OF EMBODIMENTS OF THE INVENTION

The invention provides methods of treating a patient comprising administering an effective amount of a drug composition, wherein the effective amount of the drug composition is calculated based on a pharmacokinetic-pharmacodynamic correlation (PK-PD correlation). In one embodiment, the invention provides for methods of treating a patient in need thereof (e.g., a child) with an effective amount of an oral composition that provides effective, prolonged treatment.

In one embodiment, the invention provides methods of establishing an effective amount of a drug formulation for treating an individual patient (e.g., a child) in need of treatment for a disease (e.g., ADHD or ADD). In particular, the effective amount of the oral composition can be calculated for any individual patient in need thereof (e.g., a child) based on the PK-PD correlation. The PK-PD correlation for the drug formulation can be adjusted based on a predictive factor (e.g. the weight of the patient) as a representative adjustment factor to reduce error in the PK-PD correlation. The effective amount of the composition for the individual patient in need thereof (e.g., a child) may be administered once-a-day as a single or multiple unit dose.

In some embodiments, the effective amount of the drug formulation is calculated by: measuring serum concentration at various times after dose administration for each individual in a first test population for a pharmaceutical active component in a drug formulation, generating a serum concentration profile over time for the drug formulation using the measured serum concentrations for the first test population by determining several pharmacokinetic parameters and the values of the several pharmacokinetic parameters by fitting the measured concentration values to generate a serum concentration profile, generating a pharmacokinetic equation for the drug formulation comprising the determined pharmacokinetic parameters and values, measuring a pharmacodynamic effect of the active component in the drug formulation at various times in a second test population, calculating a predicted serum concentration of the active component in the drug formulation in the second test population based on the generated pharmacokinetic equation, fitting the generated data of the pharmacodynamic effect and the predicted pharmacokinetic effect for each point in time to produce a pharmacokinetic-pharmacodynamic (PK-PD) correlation, and using the PK-PD correlation to generate a dosage chart that specifies the effective amount of the drug formulation. Presentation of the dosage information in alternative formats, such as a mobile telephone app, a website, an electronic patient care software, etc., is within the contemplation of this invention.

In some embodiments, the calculation of the predicted serum concentration of the active component in the drug formulation in the second test population based on the generated pharmacokinetic equation and the measuring of the pharmacodynamic effect of the active component in the drug formulation are used to produce a PK-PD correlation.

In some embodiments, one or more predictive factors can be included in the PK-PD correlation of the drug formulation as a representative adjustment factor to reduce error in the PK-PD correlation. In one embodiment, the predictive factor is the weight of the individual patient.

In some embodiments, the dosage chart is a printed or digital dosage chart that provides the effective amount of the dosage form for particular patients or groups of patients. In some embodiments, a physician is able to predict the effective dosage for an individual patient by consulting a dosage chart.

In some embodiments, the in vivo serum profiles of the composition are correlated to the in vitro dissolution profile of the composition. In another embodiment, a physician is able to predict the in vivo serum profile by the in vitro dissolution profile of the composition, when the weight of the patient is considered for dosing.

DETAILED DESCRIPTION OF EMBODIMENTS OF THE INVENTION

Definitions

Figure 1:
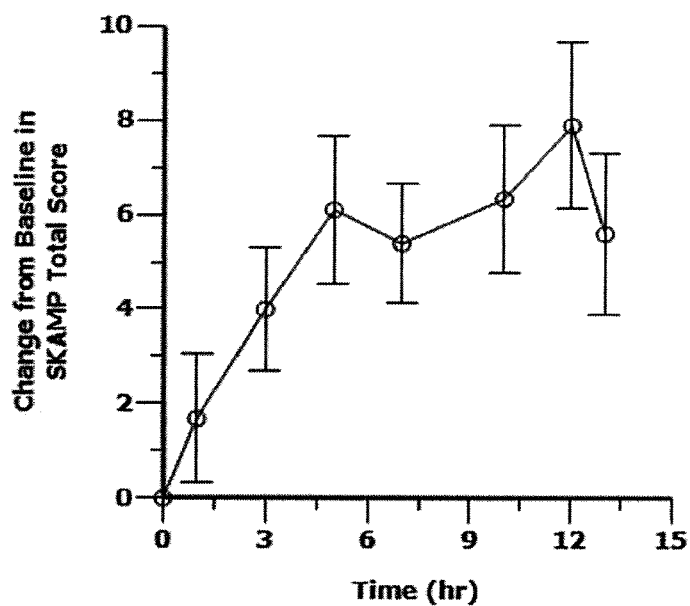
FIG. 1 shows a mean (±SE) change from baseline SKAMP total score for patients assigned to the placebo treatment (n=39)

As used herein, an "ADHD effective agent" is any agent effective to treat ADHD or ADD in any patient population (e.g., children, adolescents, adults), wherein the agent includes stimulants such as methylphenidate, and its optical isomers, or any combination that comprises at least one of these agents. As discussed herein, ADHD effective agents may also be used in the effective treatment of other conditions such as fatigue, obesity and for imparting alertness.

As used herein, an "effective amount" of the ADHD effective agent (e.g., methylphenidate) is an amount that, when administered to a patient in need, provides the desired effect on the disease pathophysiology.

As used herein, a "reference composition" is a product defined in any relevant example from WO 2013/003622, which is incorporated herein by reference.

As used herein, "controlled release" means the time course of drug appearance in medium surrounding the composition is modified compared to an immediate release composition. Controlled release encompasses "delayed release" and "extended release" formulations.

As used herein, "delayed release" means that appearance of drug in the medium surrounding the composition occurs after a time lapse. An example of a delayed release coating is a triggered-release coating.

As used herein, a "triggered-release coating" is a coating that degrades as a result of a triggering event, where the triggering event is a change in the physiological environment of surrounding the triggered-release coating. Triggering events include, but are not limited to, a pH change which occurs upon transit from one stage to another stage in a subject's gastrointestinal (GI) tract, an enzyme secreted in a particular region in a subject's GI tract, or enzymatic presence in digestion.

As used herein, "extended release" means that the rate of release is slower than the rate for an immediate release or delayed release composition from the initial point of release.

As used herein, "immediate release" means the initial period during which drug is released from the composition that does not involve delayed or extended release but may include taste-masking.

As used herein, a "subject" means any animal, but is preferably a mammal, such as, for example, a human.

As used herein, "substantially all," in the context of drug release, means 90% or more.

As used herein, "substantially similar" parameters have values within −20%/+25% of each other.

Bioavailability

Measures of bioavailability well known in the art include the area under the plasma concentration-time curve (AUC), the concentration maximum ($C_{max}$), and the time to $C_{max}$ ($T_{max}$).

AUC is a measurement of the area under the plasma concentration-time curve (e.g., serum concentration profile), and is representative of the amount of drug absorbed following administration of a single dose of a drug (see Remington: The Science and Practice of Pharmacy, (Alfonso R. Gennaro ed. 2000), page 999).

$C_{max}$ is the maximum plasma concentration achieved after oral drug administration (see Remington, page 999). An oral drug administration results in at least one $C_{max}$, but may result in more than one "peak plasma concentration" or "plasma concentration peak" (for example, following the administration of a pulsed dose formulation).

$T_{max}$ is the amount of time necessary to achieve the Cam, after oral drug administration, and is related to the rate of absorption of a drug (see Remington, page 999).

Bioequivalence can be measured by pharmacokinetic parameters such as, for example, AUC and $C_{max}$. According to the FDA, a product is bioequivalent to a reference product if the 90% confidence intervals of the relative mean AUC, $C_{max}$, and $T_{max}$ of the test formulation arc within 80% to 125% (−20%/+25%) of the reference formulation drug when administered in the fasting state. In alternative phrasing, bioequivalence is the absence of a significantly different rate and extent of absorption in the availability of the active ingredient when administered at the same dose under similar conditions. In a particular embodiment, bioequivalence may be established by comparing a test drug to a reference drug by comparing partial AUCs (e.g., over statistically or clinically relevant time intervals). This bioequivalence measure based partial AUCs may be used alone or in combination with the bioequivalence measures discussed above.

Determining an Effective Amount of a Formulation

Pharmacokinetics describes the appearance and disappearance of a drug in the patient's body; pharmacodynamics correlates the drug concentration at the site of action to the physiological effect. For both concepts, the time course after dosing is important. However, determining the effective amount of a drug formulation for a child at a given stage in the growth and development period requires determining the pharmacodynamics of the drug formulation for the child at the given stage of growth and development. More specifically, the relationship, or a correlation, between the pharmacokinetics (PK) and pharmacodynamics (PD) of a given drug formulation for the patient at the given stage of growth and development must be determined.

Traditional methods of determining the PK-PD correlation of a given drug formulation are by administering the drug formulation, and monitoring a large number of parameters in the patient. Pharmacokinetics are typically measured by drawing blood from the individual patients at several times, while monitoring the patients' pharmacodynamic results at the same times. For stimulants like ADHD medication, the pharmacodynamics results can be skewed due to the awareness and adrenaline responses associated with drug monitoring (e.g., the use of a needle to collect samples), especially in children.

The present invention relates to generating a dosage chart for an individual patient (e.g., child) by determining the pharmacokinetics of a drug formulation in a group of patients and, from that data, generating a predictive formula based on the drug dosage and the pharmacokinetic measurement over time elapsed since administration of the drug formulation. The pharmacodynamics of the drug formulation can then be measured for a group of patients, and the predictive formula for the pharmacokinetic measurement can be compared to the data from the pharmacodynamic measurements. The group of patients used to gather the pharmacokinetic data may be different from the group of patients used to gather the pharmacodynamic data. The group of patients used to gather the pharmacokinetic data may be the same group of patients used to gather the pharmacodynamic data as long as the pharmacokinetic data is gathered at a separate time from the pharmacodynamic data.

The PK-PD correlation of the drug formulation can be determined based on this comparison of the predictive formula for the pharmacokinetic measurement and the measured pharmacodynamic data over the same elapsed time since drug administration. This PK-PD correlation of the drug formulation can be used to calculate the dosing regimen for an individual patient. The dosing regimen for an individual patient may be based on predictive factors for the individual patient, such as height, weight, body mass index (BMI), volume of the systemic circulation, age, gender, etc.

The invention provides for methods of determining an effective amount of a pharmaceutical methylphenidate formulation for administration to an individual (e.g., a child). If the methylphenidate formulation is being administered to a child, the ever-changing body volume of the child as the child grows can impact the effective amount of the methylphenidate formulation for that child at any given point in the growth period. Additionally, the relative activities of various enzyme systems can change over the growth and development of the child. Accordingly, in response to these changes, the drug dosage must be changed as the child grows and develops, to continue administering an effective amount of the drug for the child over time.

Determining the Pharmacokinetics

Developing a formula to predict the pharmacokinetics of the composition is complicated because the pharmacokinetics is determined by a large number of individualized characteristics as the drug interacts with numerous different physiological entities in the body. However, surprisingly, the pharmacokinetics of the methylphenidate composition contemplated by this invention can be calculated by determining only a few parameters. Specifically, the pharmacokinetics of the methylphenidate composition can be adequately characterized using a PK model for methylphenidate plasma concentrations of compositions comprising an immediate release component and a controlled release component. Concentrations following administration of methylphenidate may be described according to the model in FIG. 2.

Where the parameters are the dose fraction absorbed via the immediate release component of the formulation (FI), the lag time of the controlled release component of the formulation ($t_{lag}$), the first-order rate constant for the immediate release component of the formulation ($Ka_{Im}$), the first-order rate constant for the controlled release component of the formulation ($Ka_{Ext}$), the apparent volume of methylphenidate distribution (V) and the apparent plasma clearance of methylphenidate (CL).

First-order elimination of methylphenidate from the central compartment adequately describes the elimination kinetics of methylphenidate from the plasma of human subjects. This elimination process can be described with a volume of distribution (V) and clearance (CL).

The selection of parameters and calculation of values for the parameters can be determined by measuring a serum concentration for each individual in a test population, and then fitting the serum concentration time data to a PK model using a nonlinear mixed-effects modeling program with first-order conditional maximum likelihood estimation to find the best set of parameter values for the observed data.

An equation developed from the structural model shown above can be determined using patient data as discussed above to describe the pharmacokinetics of the drug compositions of this invention. The pharmacokinetics of the formulation can, therefore, be calculated using only a relatively small number of parameters.

Measuring the Pharmacodynamics

The pharmacodynamics of the formulation can be determined using methods known to one of ordinary skill in the art, such as determining SKAMP, and/or PERMP scores at various times after administration of the test formulation. SKAMP scores are described in Wigal et al., *Effect of Reinforcement on Facial Responsivity and Persistence in Children with Attention-Deficit Hyperactivity Disorder*, Behavior Modification (April 1998), Vol. 22, No. 2, pp. 143-166, incorporated herein in its entirety. PERMP scores are described in Wigal et al., *Randomized, Double-Blind, Placebo-Controlled, Crossover Study of the Efficacy and Safety of Lisdexamfetamine Dimesylate in Adults with Attention-Deficit/Hyperactivity Disorder: Novel Findings Using a Simulated Adult Workplace Environment Design*, Behavioral and Brain Functions (2010), Vol. 6, p. 34, incorporated herein in its entirety.

Correlating the Pharmacokinetics and the Pharmacodynamics

In the present invention, the determination of the pharmacokinetics and the determination of the pharmacodynamics of a drug formulation do not need to be done at the same time, or on the same patient population. By not needing to take blood samples of the patients over a period of time, while studying the pharmacodynamic data, to determine the pharmacokinetics of the composition, the PK-PD correlation is not artificially skewed (e.g., by the sampling bias related to a needle producing artificial adrenaline responses).

Generating a Dosing Regimen

A dosing regimen can be generated based on a PK-PD correlation for any of the drug formulations described herein by: measuring serum concentration at various times after dose administration for each individual in a first test population for a pharmaceutical active component in a drug formulation, generating a pharmacokinetic equation describing the serum concentration profile for the drug formulation where the pharmacokinetic equation is characterized by several pharmacokinetic parameters determined by fitting the pharmacokinetic equation to the measured serum concentrations for the first test population, measuring a pharmacodynamic effect of the active component in the drug formulation at various times in a second test population, calculating a predicted serum concentration of the active component in the drug formulation in the second test population based on the generated pharmacokinetic equation, fitting the generated data of the pharmacodynamic effect and the predicted serum concentrations for each point in time to produce a PK-PD correlation, and generating a dosage chart describing the effective amount of the drug formulation.

In one embodiment, the drug formulation contains methylphenidate, and, optionally, an ion-resin.

In some embodiments, the first test population and the second test population comprise different individual subjects. The measurement of the serum concentration can be done at a different time than the measurement of the pharmacodynamic effect.

In one embodiment invention, the PK-PD correlation is further predictive of the effective amount of the composition for an individual patient in need thereof (e.g., a child) when a predictive factor is included in the calculation as a representative adjustment factor to reduce error in the PK-PD correlation. When the composition comprises methylphenidate, the predictive factor can be on or more of a patient's weight, a patient's sex, a patient's age, or systemic volume. In children, surprisingly, the predictive factor of weight alone was sufficient to adequately reduce the error in the PK-PD correlation (without needing to factor in other covariates such as body-mass index (BMI), sex, age, etc.).

In some embodiments, the physician can establish a dosing regimen for an individual patient based on the PK-PD correlation, and, optionally, based on the predictive factor for the individual patient. The dosing regimen for an individual patient can be individualized by one or more predictive factors for that individual patient. In a particular embodiment, the physician administers to a patient an effective amount of a formulation that provides the in vivo release profiles described herein, wherein the effective amount is based on the PK-PD correlation and a predictive factor, wherein the predictive factor is the patient's weight, the patient's age, or a combination of the patient's weight and sex.

In some embodiments, a dosage chart can be formulated using the methods described herein. In one embodiment, a dosage chart can be formulated by determining the pharmacokinetics of a formulation (e.g., calculating F1, $t_{lag}$, $Ka_{Im}$, $Ka_{Ext}$, V, and CL), determining the pharmacodynamics of the formulation (e.g., measuring the SKAMP or PERMP scores), generating a PK-PD correlation based on a predictive factor (e.g., weight of the individual patient), and determining the effective dose for an individual patient based on the output.

In some embodiments, the chart may describe the amount of methylphenidate hydrochloride equivalent in relation to the body weight of the patient. A physician can consult the chart to provide an effective amount of the drug formulation to administer to the patient based on the body weight of the patient. The dosage chart can be contained in various mediums, including paper, digital storage media, eInk, etc.

In some embodiments, the pharmacodynamic measurement is a psychological measurement, that may relate to measuring pain, sleep, attention, impotence, or measurements related to disorders of the central nervous system.

In some embodiments, a patient in need thereof (e.g., a child) is provided with an effective amount of an ADHD-effective agent in accordance with a dosage chart. In some embodiments, the patient in need thereof (e.g., the child) is provided with an effective amount of the formulation based on the following table:

| Body Weight Range | | Amount of Methylphenidate•HCl equivalent |
|---|---|---|
| <12 kg | <26 lb | 10 mg |
| 12-33 kg | 26-73 lb | 20 mg |
| 33-55 kg | 73-121 lb | 30 mg |
| 55-77 kg | 121-169 lb | 40 mg |
| 77-99 kg | 169-218 lb | 50 mg |
| >99 kg | >218 lb | 60 mg |

In some embodiments, a physician may prescribe a dose of methylphenidate for a patient in need thereof (e.g., a child) for the treatment of ADHD by: determining the body weight of the patient, referring to the chart above that correlates body weight ranges with a number of dosage amounts having a different level of methylphenidate, identifying the corresponding dosage amount to the body weight of the patient, and administering to the patient the dosage amount.

The invention provides for methods of treating a patient in need thereof (e.g., a child) with an effective amount of an ADHD-effective agent (e.g., methylphenidate) where the ADHD-effective agent is formulated to provide the in vivo release profile described herein. Methylphenidate formulations which have in vivo release profiles suitable for the present invention are described in one or more of the following: U.S. Pat. Nos. 4,221,778; 4,996,047; 5,980,882; 6,605,300; 6,913,768; 8,846,100; 6,344,215; 8,747,902; 8,465,765; 8,999,386; 8,883,213; 6,930,129; 6,228,398; 6,673,367; and 6,419,960; U.S. Publication Nos. 2003/0099711; 2006/0193877; 2007/0059270; 2007/01400983; 2007/0148239; US 2007/0264323; and 2009/0011027. The disclosure of each of these patents and publications is incorporated by reference herein in their entireties.

The invention provides methods of treating a patient in need thereof (e.g., a child) with compositions having various drug (e.g., ADHD effective agent) release profiles. In particular, the compositions may be administered in the morning and have therapeutically effective activity throughout the course of the day. For example, in one embodiment, the composition is administered to a child during breakfast (i.e., before school starts) and, by the time school starts, the ADHD effective agent (e.g., methylphenidate) will begin having a therapeutic effect on the child. The composition will continue to be therapeutically effective throughout the day including the mid-afternoon, when children tend to be fatigued. As such, the compositions described herein typically have an escalating in vivo serum profile early in the therapeutic time course.

In one embodiment, the patient in need thereof (e.g., a child) is administered a composition having an in vivo serum profile bioequivalent to the profile of a reference composition. In another other embodiment, the composition has one or more parameters (e.g., at least one, at least two, at least three, at least four, at least five, at least six, at least seven, at least eight, at least nine, at least ten, or eleven parameters) selected from $AUC_{0-4}$, $AUC_{0-5}$, $AUC_{4-12}$, $AUC_{5-12}$, $AUC_{5-t}$($AUC_{5-last}$), $AUC_{0-12}$, $AUC_{0-24}$, $AUC_{0-t}$, $AUC_{0-\infty}$, $C_{max}$, and/or $T_{max}$ which meet the bioequivalence conditions for a reference composition.

In some embodiments, the invention provides for methods of treating a patient in need thereof (e.g., a child) by providing compositions in which the rate of appearance of the ADHD effective agent (e.g., methylphenidate) in a dissolution medium increases after a period of decrease in the rate of appearance of the drug in the dissolution medium. The compositions typically contain an immediate release and delayed release portion. The immediate release portion, in an in vitro dissolution assay, contributes to an initial release of ADHD effective agent (e.g., 30-60%) within an initial time period (e.g., 0.5, 1, 1.5, 2, or 2.25 hours from when the composition is introduced into the dissolution medium). After the initial increase amount of ADHD effective agent in the dissolution, due to the immediate release portion, the release rate of ADHD effective agent will decrease or level off. After this decrease or leveling off, typically the delayed release portion will release and the amount of ADHD effective agent released increases until, e.g., 80% or more of the ADHD effective agent is released. It will be appreciated that the first and second time points will vary depending on the ADHD effective agent, coatings used, and ratio of immediate and delayed release components of the composition.

In a particular embodiment, 30-33% of the drug (e.g., ADHD effective agent such as methylphenidate) is released the first 30 minutes after the composition is introduced into a dissolution assay, 34-42% of the drug is released within 30 minutes to 2 hours, 40-80% of the drug is released within 2 to 4 hours and 80-100% of the drug is released within 4 to 24 hours. For any of these embodiments, the conditions of the dissolution assay may be an initial dissolution medium of 0.1 NHCL, and after 2 hours, the medium is adjusted to a pH which triggers the triggered release coating, e.g., pH of ~6.8; and dissolution testing is performed using a USP Apparatus 2. In other embodiments, the pH is adjusted to e.g., pH 6.8, 7, etc.

The invention also provides for methods of treating a patient in need thereof (e.g., a child) by providing compositions in which the composition achieves an ascending plasma concentration of the drug (e.g., methylphenidate during a time period) after a therapeutically effective level is reached. Typically, a therapeutically effective level is reached within one, two, or three hours after ingestion of the composition. Sometime after the therapeutically effective level is reached, the plasma concentration of drug increases due to additional release of drug from the composition to a peak drug concentration level. In some individuals, clearance of drug will result in a decrease in plasma level between these two releases, resulting in two successive peak drug levels. In others, the timing of the two releases is close enough that no decrease is observed. As a result, the in vivo plasma concentration profile is preferably bimodal with two peaks. For example, the first peak may be achieved, between 1 to 3, 1 to 2.5, or 1 to 2 hours after ingestion of the composition. The second peak may be achieved 4 to 7, 4 to 6, or 4 to 5 hours after ingestion of the composition. The first or second peak may be the $C_{max}$. Alternatively, the composition may have an in vivo serum profile that reaches a therapeutically effective level fairly rapidly (1-3 hours) and them continues to increase more slowly up to a maximum serum level between 4 hours and 7 hours after ingestion. It will be appreciated that the therapeutic and peak drug concentration level will vary depending on the subject, drug, coatings used, and ratio of coatings.

The compositions administered to the patient in need thereof (e.g., a child) may include various coatings and components (e.g., particles coated with a delayed release coating, particles coated with an extended release coating, particles coated with an sustained release coating, etc.).

The formulation that provides the in vivo release profiles described herein may include components of any of the following: a delayed release component (e.g., contains delayed release coating), an immediate release component (e.g., an uncoated component), an extended release component, a sustained release component (e.g., comprising a water-insoluble, water-impermeable, pH independent, barrier coated ion-exchange resin complex), a modified release component (e.g., comprising a matrix), or combinations thereof. Suitable formulations are described in U.S. Pat. Nos. 4,221,778; 4,996,047; 5,980,882; 6,605,300; 6,913,768; 8,846,100; 6,344,215; 8,747,902; 8,465,765; 8,999,386; 8,883,213; 6,930,129; 6,228,398; 6,673,367; and 6,419,960; U.S. Publication Nos. 2003/0099711; 2006/0193877; 2007/0059270; 2007/01400983; 2007/0148239; US 2007/0264323; and 2009/0011027, the formulation disclosures of which are incorporated herein in their entirety.

In some embodiments, a physician is assisted in prescribing a dose of methylphenidate for the treatment of attention deficit hyperactivity disorder (ADHD) in an individual patient by a method comprising: determining the body weight of said individual patient; referring to a chart or reference tool that correlates a plurality of body weight ranges with a corresponding number of dosage amounts, each having a different level of methylphenidate; identifying a single dosage amount corresponding to a particular weight range in which said individual patient's weight falls in the chart or reference tool; and administering to said individual patient the identified dosage amount. The individual dosage amount can be based on the following chart:

| Body Weight Range | | Amount of Methylphenidate•HCl equivalent |
| --- | --- | --- |
| <12 kg | <26 lb | 10 mg |
| 12-33 kg | 26-73 lb | 20 mg |
| 33-55 kg | 73-121 lb | 30 mg |
| 55-77 kg | 121-169 lb | 40 mg |
| 77-99 kg | 169-218 lb | 50 mg |
| >99 kg | >218 lb | 60 mg |

EXAMPLES

Example 1

This example describes the development of a pharmacokinetic-pharmacodynamic model for the therapeutic effect of a particular methylphenidate formulation and its testing on a population of pediatric patients with ADHD. The drug formulation tested in this example is designated MPH XR-ODT and described in U.S. Publication No. 2014/0030348, which is incorporated herein by reference.

Figure 2:
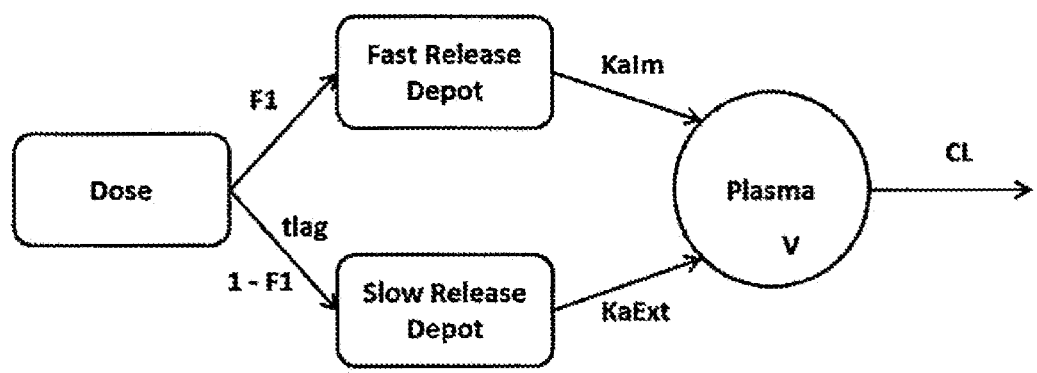
FIG. 2 shows a structural PK model for plasma concentration of a drug administered in a composition formulated as an immediate release component plus a controlled release component.

The structural PK model for a plasma concentration following administration of the stimulant was described by two parallel inputs into a central compartment and linear elimination from the central compartment. This can be described graphically as shown in FIG. 2.

The fast release depot represents the immediate release portion of the formulation that is readily absorbed into the plasma using a first-order rate constant (KaIm). The fraction of dose released from an immediate release coating was estimated with the relative bioavailability parameter (F1).

The slow release depot represents an extended release core that slowly releases drug following water permeation into the product core. The slow release was presumed to follow first-order absorption kinetics (KaExt). The time required for water to permeate a product core was represented with a lag time (tlag). The fraction of dose released from an extended release core was estimated as 1-F1.

First-order elimination from the central compartment appears to be adequately describe the elimination kinetics of the stimulant from the plasma. This elimination process was described with a volume of distribution (V) and clearance (CL).

Body weight appears as a covariate of CL and V which was included in the model in the following way:

$$CL_i = tvCL * Weight^{0.655} \qquad \text{Equation 1}$$

$$V_i = tvV * Weight^{0.670} \qquad \text{Equation 2}$$

where CL, and V, are the clearance and volume of distribution parameters for individual "i", tvCL and tvV are the typical population clearance and volume of distribution parameters, and weight is body weight in kg. Model parameters were determined using nonlinear mixed-effects modeling with first-order conditional maximum likelihood estimation using Phoenix NLME (Version 6.3).

The SKAMP total score data showed that over the 13 hour classroom evaluation, there appeared to be a gradual increase in the SKAMP total score over time. This phenomenon was readily obvious in the patients that were assigned to the placebo treatment arm. Therefore, the PD model required a drug effect component and a placebo effect component.

The basic PD model was described by the following equation:

$$E = BSL - DE + PE \qquad \text{Equation 3}$$

where E is the observed SKAMP total score, BSL is the SKAMP total score just prior to dose administration under the classroom setting on Day 7 (Visit 8), DE is the reduction in SKAMP total score due to the presence of methylphenidate, and PE is the increase in SKAMP total score due to the placebo or classroom procedures.

The drug effect (DE) was modeled using an $E_{max}$ equation as shown below:

$$DE = \frac{E_{max} * C_p}{EC_{50} + C_p} \qquad \text{Equation 4}$$

where $E_{max}$ is the maximum decrease in SKAMP total score, $C_p$ is the plasma methylphenidate concentration, and $EC_{50}$ is the concentration of methylphenidate required to elicit 50% of the maximal reduction in SKAMP total score. Using this model, the drug effect starts at zero when $C_p$ is zero. Increases in $C_p$ create a linear increase in the drug effect while $C_p$ is less than $EC_{50}$. Once $C_p$ is greater than $EC_{50}$, the total drug effect asymptotically approaches the maximal response defined by $E_{max}$.

The placebo effect (PE) was modeled using a linear equation as shown below:

$$PE = Slope * t \qquad \text{Equation 5}$$

where Slope is the rate of change in SKAMP total score with time, and t is the time after dose administration. While a variety of models were evaluated, this linear model was adequate to fit the observed data from the patients assigned to the placebo treatment.

Thus the final structural PD model utilized in the analysis is shown below:

$$E = BSL - \left(\frac{E_{max} * C_p}{EC_{50} + C_p}\right) + (Slope * t) \qquad \text{Equation 6}$$

Linking PK and PD Structural Models

The PK and PD structural models were linked using a direct effect model. In a direct effect model, the effect directly correlated to the measured plasma concentrations of the drug. Plasma sampling for determination of methylphenidate concentrations was not performed, due to the potential impact of multiple venipunctures on the efficacy outcomes. The addition of plasma sampling procedures is expected to cause anxiety for the pediatric patients, and it would negatively affect the SKAMP Combined score. Because of the potential effect of blood sampling during a classroom evaluation, a modeling and simulation analysis was conducted in place of blood sampling in the pediatric patients. Therefore, the plasma methylphenidate concentration-time profile was simulated for each patient in the study using the previously described pediatric PK model, and the final PK model parameter estimates. The simulated methylphenidate concentrations were then used to estimate the SKAMP Combined score using the PD structural model described above. As this was an integrated PKPD model, the simulation of plasma methylphenidate concentrations and the estimation of the PD parameters occurred during a single minimization procedure.

PK/PD Statistical Model

The PK/PD mixed-effects model has two components:

A structural model that characterizes the effect-concentration-time relationship, and A random effects model containing between individual variability in the pharmacodynamic parameters, and a residual error component that accounts for within individual variability and measurement errors.

In the development of the random effects model, all parameters were assumed to be log-normally distributed and exponential between individual variability terms were included on the pharmacokinetic parameters found in the model. The form of the exponential error model is shown in Equation 7, $$P_i = P * e^{\eta_i^P} \qquad \text{Equation 7}$$

where:
$P_i$=the true parameter value for individual i
P=the typical value (population mean) of the parameter
$\eta_i^P$ the difference between the true value for individual I and the typical value for the population, with a mean of 0 and a variance of $\omega^2$ For the purpose of this analysis, additive (Equation 8) and proportional (Equation 9) residual error models were evaluated.

$$C_{ij} = \widehat{C}_{ij} + \epsilon_{1ij} \qquad \text{Equation 8}$$

$$C_{ij} = \widehat{C}_{ij} * (1 + \epsilon_{2ij}) \qquad \text{Equation 9}$$

where:

$C_{ij}$=the jth measured concentration for individual i $\hat{C}_{ij}$=the jth model predicted concentration for individual i $\varepsilon_{1ij}$=the additive residual error for the jth concentration for individual I, and is normally distributed with a mean of 0 and a variance of $\omega_2^2$.

$\varepsilon_{2ij}$=the proportional residual error for the jth measurement for individual I, and is normally distributed with a mean of 0 and a variance of $\omega_1^2$.

Hypothesis testing was performed using the likelihood-ratio test to discriminate among alternative hierarchical models. When comparing alternative models, the difference in the objective function is approximately chi-square distributed with n degrees of freedom, where n is the difference in the number of parameters between the hierarchical models. A decrease of 6.64 in the value of the objective function value (which is minus twice the maximum logarithm of the likelihood of the data) is significant under the likelihood-ratio test (n=1, p<0.01). A decrease of 10.83 in the value of the objective function value is significant under the likelihood-ratio test (n=1, p<0.001). Goodness of fit was evaluated using diagnostic scatter plots. No covariates were evaluated in this analysis.

Results

The final analysis dataset for the PKPD model contained 640 SKAMP total score measurements from 81 pediatric patients. There were 53 (65.4%) male patients in the analysis dataset, and 42 (51.9%) patients received the formulation and the remaining 39 (48.1%) patients received placebo during the Day 7 classroom evaluation. The distribution of patients across the formulation dose range is shown in Table 1.

TABLE 1

Number of Patients at Each Dose Level and Treatment

| Optimal Dose Level (mg/day) | Number of Patients on Day 7 (Visit 8) | |
| --- | --- | --- |
| | Active Treatment | Placebo Treatment |
| 20 mg/day | 6 | 4 |
| 30 mg/day | 12 | 8 |
| 40 mg/day | 11 | 12 |
| 60 mg/day | 13 | 15 |
| Total | 42 | 39 |

PKPD Model—Base Model

The integrated PKPD model with the PK and PD structural models was fit to the SKAMP total score measurements. The base PKPD model consists of 4 structural parameters, 3 between individual variability parameters, and a residual error parameter. These parameters are described below, respectively:

Slope represents the change in SKAMP total score per hour during the 13-hour classroom session E0 represents the SKAMP total score at time=0, just prior to dose administration (which is also 24 hours after administration of the previous dose)

EC50 is the concentration of methylphenidate required to achieve 50% of the maximal reduction in SKAMP total score Emax is the maximum reduction in SKAMP total score with administration of methylphenidate Between individual variability parameters were included on E0, EC50 and Slope Residual error was modeled using an additive error parameter A placebo model was included after reviewing the mean Change from Baseline in SKAMP total score for patients in the placebo treatment arm (FIG. 1). Over the 13-hour classroom session, the SKAMP score tended to increase in the absence of any treatment intervention. The reason for this increase is not known; however, it is critical to include this change in response in the PKPD model to accurately depict changes in SKAMP total score.

See FIG. 1: Mean (+SE) Change from Baseline SKAMP Total Score for Patients Assigned to the Placebo Treatment (n=39).

Linear, polynomial, and Emax models were fit to the placebo treatment data. The linear model provided the best overall fit and fewest parameters, therefore the linear placebo model was included in the base PKPD model. Final parameters and variability estimates for the base PKPD model are shown in Table 2.

TABLE 2

Base PKPD model parameter estimates

| Structural model parameters | Estimate (% CV) |
| --- | --- |
| Slope (1/h) | 0.691 (12.1%) |
| E0 | 21.9 (5.0%) |
| EC50 (ng/mL) | 14.24 (28.7%) |
| Emax | 38.1 (12.5%) |

| Between individual variability parameters | Estimate (% Shrinkage) |
| --- | --- |
| ωSlope | 0.365 (30.6%) |
| ωE0 | 0.154 (8.0%) |
| ωEC50 | 0.157 (63.0%) |

| Residual variability parameter | Estimate (% CV) |
| --- | --- |
| ε (additive) | 5.70 (3.5%) |

% CV = percentage coefficient of variation calculated as standard deviation/estimate * 100
% Shrinkage = percentage shrinkage to mean parameter estimate calculated as 1 − standard deviation/estimate*100

All structural model parameters except $EC_{50}$ were estimated with good precision, as shown by the percentage coefficient of variation of 12.5% or less. The percentage coefficient of variation or $EC_{50}$ was 28.7%. The between individual variability parameter for E0 was small, but the between individual variability parameter for Slope and $EC_{50}$ were large (shrinkage of 30.6% and 63.0%, respectively). Residual variability (5.70) was moderately large relative to baseline SKAMP scores (21.9).

The diagnostic plots showed a good fit of the base PKPD model to the SKAMP total score observations. Residuals were uniformly distributed with time and methylphenidate concentrations with no obvious bias.

PKPD Model—Covariate Model

Individual values for the covariates BMI, sex, weight, age, race and ethnicity were explored graphically by plotting the covariates on the x-axis and the ETA ($\eta_i^P$) for each pharmacodynamic parameter. The ETA represents the difference between the individual PD response estimate and the typical value for the entire population. Relationships between the covariate and ETA suggest that the variations in individual parameter estimates may be explained by differences in the covariates between subjects. Two potential covariates emerged from the graphical exploration: Age as a covariate for E0 and weight as a covariate for E0. In pediatric patients, age and weight are collinear because weight tends to increase with age. Both covariates (age and weight) were added to the base PKPD model, and both resulted in statistically significant reductions in the objective function value, with weight being a more significant covariate. In both models, subjects with higher weights or ages tended to have lower baseline SKAMP total scores. Other parameters (EC50, Emax, Slope and residual error) were unchanged.

The objective of this analysis is to model the effect of methylphenidate on the SKAMP total score. While the finding that baseline SKAMP total scores are lower in older and heavier pediatric patients is statistically significant, the inclusion of a covariate on a baseline parameter does not provide additional information about the effects of methylphenidate. Therefore, these covariates were not included, and the Base PKPD model was considered the Final PKPD model.

Posterior Predictive Check of Final PKPD Model

A posterior predictive check was performed on the final PKPD model. The posterior predictive check suggests that the final PKPD model can accurately predict the SKAMP total score over the 13-hour classroom test period.

Simulations

The final PKPD model was used to perform simulations of SKAMP total scores in pediatric patients. At each dose strength, 500 separate simulated profiles were produced across the weight range 15-80 kg. Simulated SKAMP total score data was divided by dose level and body weight as shown in Table 3:

TABLE 3

MPH XR-ODT Dose Levels and Patient Body Weight Groups

| MPH XR-ODT Dose Levels | Patient Body Weight Groups[1) |
|---|---|
| 10 mg, 20 mg, 30 mg, 40 mg, 50 mg, 60 mg | 5 kg, 10 kg, 15 kg, 20 kg, 25 kg, 30 kg, 35 kg, 40 kg, 45 kg, 50 kg, 55 kg, 60 kg, 65 kg, 70 kg, 75 kg, 80 kg, 85 kg, 90 kg, 95 kg |

[1)]Body weight groups are defined by the median of the range of body weights. For example, the 20 kg group includes individuals between 17.5 kg and <22.5 kg, and the 25 kg group includes individuals between 22.5 and <27.5 kg.

The mean SKAMP total score profiles for each MPH XR-ODT dose level was plotted by body weight. As expected, MPH XR-ODT dose levels ≥40 mg provide the greatest reduction in SKAMP total score for nearly all body weights. Interestingly, at body weights ≤45 kg, there is little differentiation between the response at the 40-60 mg dose levels. Beginning at 45 kg, a separation is observed with the 10 mg and 20 mg dose levels providing little to no reduction in SKAMP total score, while significant reductions are observed with the 40-60 mg dose levels. Thus, the shape of the dose-response curve varies as body weight changes.

For each simulated SKAMP total score profile, the maximum decrease from baseline SKAMP total score was calculated and those maximum changes were summarized by dose level and body weight. From this data, it is clear that greater reductions in SKAMP total scores are observed with higher doses at a constant body weight (i.e., lines slope downward from left to right). Similarly, for a given dose strength, pediatric patients with lighter body weight experience a greater reduction in SKAMP total score than heavier patients at the same dose level (i.e., line for 15 kg body weight is below line for 80 kg body weight).

The mean baseline SKAMP total score was approximately 22 (E0 estimate of 21.99, Table 2). Therefore a decrease of 20 points in the SKAMP total score would represent a near complete reversal of the symptoms for the average patient, as measured by SKAMP. The data in Table 4 clearly show that patients who are heavier generally require a larger MPH XR-ODT dose. In addition, the beneficial effects of methylphenidate appear to plateau at higher doses in subjects such that increasing the MPH XR-ODT dose may not provide increased symptom control in some patients.

TABLE 4

Percent of Simulation Patients with a SKAMP Total Score Decrease > 20

| Weight Group | Percent of Simulated Patients by MPH XR-ODT Dose Level | | | | | |
|---|---|---|---|---|---|---|
| | 10 mg | 20 mg | 30 mg | 40 mg | 50 mg | 60 mg |
| 5 kg | 53.3 | 70.0 | 88.2 | 100.0 | 88.9 | 100.0 |
| 10 kg | 37.8 | 75.0 | 83.3 | 100.0 | 96.4 | 97.1 |
| 15 kg | 23.8 | 58.6 | 86.4 | 96.6 | 96.2 | 97.0 |
| 20 kg | 15.8 | 64.0 | 69.7 | 83.3 | 75.0 | 92.9 |
| 25 kg | 7.4 | 23.5 | 70.0 | 72.4 | 77.8 | 88.0 |
| 30 kg | 8.0 | 48.6 | 57.7 | 75.9 | 80.0 | 88.9 |
| 35 kg | 15.8 | 30.4 | 59.3 | 51.9 | 66.7 | 95.5 |
| 40 kg | 25.9 | 23.8 | 40.5 | 55.6 | 74.1 | 84.4 |
| 45 kg | 15.4 | 28.6 | 52.2 | 68.2 | 55.0 | 69.0 |
| 50 kg | | 20.8 | 17.2 | 53.3 | 76.0 | 70.8 |
| 55 kg | 12.1 | 20.7 | 36.0 | 50.0 | 55.2 | 93.1 |
| 60 kg | 7.7 | 20.0 | 44.0 | 47.6 | 60.0 | 76.9 |
| 65 kg | 6.3 | 18.2 | 25.0 | 48.4 | 50.0 | 58.3 |
| 70 kg | | 4.2 | 34.5 | 50.0 | 53.1 | 64.3 |
| 75 kg | 11.1 | 22.6 | 30.4 | 42.9 | 66.7 | 38.5 |
| 80 kg | | 20.0 | 26.1 | 39.3 | 60.0 | 73.1 |
| 85 kg | 3.6 | 6.7 | 29.2 | 34.8 | 44.4 | 64.7 |
| 90 kg | 9.4 | 9.1 | 15.8 | 26.9 | 53.6 | 59.1 |
| 95 kg | 9.1 | 4.0 | 35.3 | 36.4 | 60.0 | 63.0 |

Note:
Values ≥ 50% are in boldface font.

Assuming that the target MPH XR-ODT dose should provide a SKAMP Combined score reduction >20 in at least 50% of subjects, the optimal MPH XR-ODT doses by body weight can be determined. A linear regression of those optimal doses versus body weight from the simulations was performed. The optimal doses for a range of body weights from 7-100 kg is presented in Table 5.

TABLE 5

Optimal MP 11 XR-ODT Dose by Body Weight

| Body Weight Range | Amount of Methylphenidate•HCl equivalent |
|---|---|
| <12 kg | <26 lb | 10 mg |
| 12-33 kg | 26-73 lb | 20 mg |
| 33-55 kg | 73-121 lb | 30 mg |
| 55-77 kg | 121-169 lb | 40 mg |
| 77-99 kg | 169-218 lb | 50 mg |
| >99 kg | >218 lb | 60 mg |

The invention claimed is:

1. A method of treating an individual patient comprising administering to said individual patient a therapeutically effective amount for said patient of an oral dose form containing an ADHD-effective agent, wherein the oral dose form has an in vitro profile of: 30-33% of the ADHD-effective agent is released within the first 30 minutes after the oral dose form is introduced into an in vitro dissolution assay, 34-42% of the agent is released within 2 hours, 40-80% of the agent is released within 4 hours, and 80-100% of the agent is released within 24 hours, wherein conditions of the dissolution assay are an initial dissolution medium of 0.1 N HCl, and after 2 hours, the medium is adjusted to a pH of about 6.8; and the dissolution assay is performed using a USP Apparatus 2, wherein, for in vivo pharmacokinetic parameters of the oral dose form, at least one in vivo pharmacokinetic parameters selected from the group consisting of $C_{max}$, $AUC_{0-5}$, $AUC_{5-12}$, $AUC_{5-24}$, $AUC_{5-1}$, $AUC_{0-12}$, $AUC_{0-24}$, $AUC_{0-t}$, and $AUC_{0-\infty}$ have a 90% confidence interval with upper and lower bounds within a range from 80%-125% of the value of the same parameter(s) for a bioequivalent reference composition, wherein the oral dose form comprises:
(a) a sustained release racemic methylphenidate component comprising a water-insoluble, water permeable, pH-independent barrier coated, racemic methylphenidate-ion exchange resin complex in a polymeric matrix, wherein said barrier coating is over the racemic methylphenidate-ion exchange resin complex-matrix;
(b) a first immediate release component which comprises an immediate release uncoated racemic methylphenidate-ion exchange resin complex; and
(c) a second immediate release racemic methylphenidate component which comprises an uncomplexed racemic methylphenidate, and wherein the therapeutically effective amount of the oral dose form is correlated to the body weight of said individual patient as follows:

| Body Weight Range | | Amount of Methylphenidate•HCl equivalent |
|---|---|---|
| <12 kg | <26 lb | 10 mg |
| 12-33 kg | 26-73 lb | 20 mg |
| 33-55 kg | 73-121 lb | 30 mg |
| 55-77 kg | 121-169 lb | 40 mg |
| 77-99 kg | 169-218 lb | 50 mg |
| >99 kg | >218 lb | 60 mg |

2. A method of assisting a physician in prescribing a dose of methylphenidate formulated in the oral dose form of claim 1 for the treatment of attention deficit hyperactivity disorder (ADHD) in an individual patient, comprising:
a. determining the body weight of said individual patient;
b. referring to a chart or reference tool that correlates a plurality of body weight ranges with a corresponding number of dosage amounts each having a different level of methylphenidate;
c. identifying a single dosage amount corresponding to a particular weight range in which said individual patient's weight falls in the chart or reference tool; and
d. administering to said individual patient the identified dosage amount, wherein the chart or reference tool includes the following correlations between body weight range and said dosage amount of methylphenidate hydrochloride equivalent:

| Body Weight Range | | Amount of Methylphenidate•HCl equivalent |
|---|---|---|
| <12 kg | <26 lb | 10 mg |
| 12-33 kg | 26-73 lb | 20 mg |
| 33-55 kg | 73-121 lb | 30 mg |
| 55-77 kg | 121-169 lb | 40 mg |
| 77-99 kg | 169-218 lb | 50 mg |
| >99 kg | >218 lb | 60 mg |

* * * * *